United States Patent
Mao (10) Patent No.: US 12,138,122 B2
(45) Date of Patent: Nov. 12, 2024

(54) ULTRASONIC PROBE AND ULTRASONIC DETECTING DEVICE PROVIDED WITH SAME

(71) Applicant: WUXI HISKY MEDICAL TECHNOLOGIES CO., LTD., Wuxi (CN)

(72) Inventor: Junwei Mao, Wuxi (CN)

(73) Assignee: WUXI HISKY MEDICAL TECHNOLOGIES CO., LTD. WUXI (CN), Wuxi (CN)

(*) Notice: Subject to any disclaimer, the term of this patent is extended or adjusted under 35 U.S.C. 154(b) by 505 days.

(21) Appl. No.: 16/120,183

(22) Filed: Aug. 31, 2018

(65) Prior Publication Data
US 2018/0368809 A1    Dec. 27, 2018

Related U.S. Application Data (63) Continuation of application No. PCT/CN2016/092857, filed on Aug. 2, 2016.

(30) Foreign Application Priority Data

Apr. 22, 2016    (CN) .......................... 201610257070.4

(51) Int. Cl.
*A61B 8/00*    (2006.01)
*A61B 8/06*    (2006.01)
(Continued)

(52) U.S. Cl.
CPC ............. *A61B 8/4494* (2013.01); *A61B 8/06* (2013.01); *A61B 8/08* (2013.01); *A61B 8/0833* (2013.01);
(Continued)

(58) Field of Classification Search
CPC ....... A61B 8/4494; A61B 8/08; A61B 8/0833; A61B 8/06; A61B 8/4444; A61B 8/4488;
(Continued)

(56) References Cited

U.S. PATENT DOCUMENTS 5,606,971 A * 3/1997 Sarvazyan ......... G01N 29/2456
600/587
2007/0016031 A1  1/2007 Mourad et al.
(Continued)

FOREIGN PATENT DOCUMENTS

CN    101600392 A    12/2009
EP    3446635 A1    2/2019
(Continued)

OTHER PUBLICATIONS

Second Office Action of the parallel CA application.
(Continued)

*Primary Examiner* — Angela M Hoffa
*Assistant Examiner* — Younhee Choi
(74) *Attorney, Agent, or Firm* — J.C. PATENTS (57) ABSTRACT

An ultrasonic probe and an ultrasonic detecting device provided with the ultrasonic probe. The ultrasonic probe includes: an ultrasonic transducer array configured to transmit and receive ultrasonic waves; a conducting device disposed at the front end of the ultrasonic transducer array, and the conducting device includes a fluid chamber filled with fluid. The fluid chamber has an opening and an energy receiving port which are in communication with each other, and the opening is disposed on a front surface of the conducting device and covered by an elastic film; an energy applying device, connected to the energy receiving port to apply energy to the fluid within the fluid chamber to make the elastic film vibrate so as to generate a shear wave.

18 Claims, 5 Drawing Sheets

(51) Int. Cl.
  *A61B 8/08* (2006.01)
  *B06B 1/06* (2006.01)
  *B06B 1/02* (2006.01)
(52) U.S. Cl.
  CPC .......... *A61B 8/4444* (2013.01); *A61B 8/4488* (2013.01); *A61B 8/485* (2013.01); *B06B 1/0622* (2013.01); *B06B 1/0666* (2013.01); *B06B 1/02* (2013.01)
(58) Field of Classification Search
  CPC .......... A61B 8/485; A61B 8/085; A61B 8/44; A61B 8/4483; A61B 8/4477; A61B 8/54; B06B 1/0666; B06B 1/0622; B06B 1/02; B06B 1/18; B06B 1/20; G01R 33/56358
  See application file for complete search history.

(56) References Cited

U.S. PATENT DOCUMENTS

| | | | |
|---|---|---|---|
| 2008/0015551 A1* | 1/2008 | Feine | A61B 17/320068 606/1 |
| 2008/0058644 A1* | 3/2008 | Sandrin | A61B 8/4209 600/459 |
| 2012/0038242 A1* | 2/2012 | Tanaka | B06B 1/0292 310/300 |
| 2013/0058195 A1* | 3/2013 | Cloutier | A61B 8/085 367/99 |
| 2015/0005631 A1* | 1/2015 | Jeong | A61B 8/485 600/438 |
| 2015/0080926 A1 | 3/2015 | Emery | |
| 2015/0351642 A1* | 12/2015 | Sliwa | A61B 5/02007 600/427 |
| 2016/0007968 A1* | 1/2016 | Sinkus | G01R 33/56358 600/407 |
| 2016/0089110 A1 | 3/2016 | Milkowski et al. | |
| 2016/0287909 A1* | 10/2016 | Maxwell | A61N 7/00 |
| 2018/0368809 A1 | 12/2018 | Mao | |

FOREIGN PATENT DOCUMENTS

| | | | | |
|---|---|---|---|---|
| JP | 2006-201666 A | 8/2006 | | |
| JP | 4151888 B2 | 9/2008 | | |
| JP | 2010-516372 A | 5/2010 | | |
| JP | 2011-504230 A | 2/2011 | | |
| KR | 20150077049 A | * 7/2015 | .......... | A61B 8/4444 |
| KR | 20160037790 A | 4/2016 | | |
| RU | 2 499 560 C1 | 11/2013 | | |
| WO | 2006/041050 A1 | 4/2006 | | |
| WO | WO-2008090504 A1 | * 7/2008 | .......... | A61B 8/4281 |
| WO | WO-2013017105 A1 | * 2/2013 | ............ | A61B 8/485 |
| WO | 2014/208199 A1 | 12/2014 | | |
| WO | 2017/181553 A1 | 10/2017 | | |
| WO | WO2017181553 | 10/2017 | | |

OTHER PUBLICATIONS

The Supplementary European Search Report of corresponding European application No. 16 89 9140, dated Nov. 8, 2019.
The Canadian Examination Report of corresponding Canada application No. 3,017,627, dated Jul. 12, 2019.
The first Office Action of the parallel ID application.
The third OA of CA application No. 3,017,627.
The forth OA of CA application No. 3,017,627.

* cited by examiner

ULTRASONIC PROBE AND ULTRASONIC DETECTING DEVICE PROVIDED WITH SAME

CROSS-REFERENCE TO RELATED APPLICATIONS

This present application is a continuation of International Application No. PCT/CN2016/092857, filed on Aug. 2, 2016, which claims priority to Chinese Patent Application No. 201610257070.4, filed on Apr. 22, 2016, both of which are hereby incorporated by reference in their entireties.

TECHNICAL FIELD

The present disclosure relates to the field of ultrasonic detecting technologies, and in particular to an ultrasonic probe and an ultrasonic detecting device provided with the ultrasonic probe.

BACKGROUND

Instantaneous elastography is a rapidly developing non-invasive diagnostic technique that utilizes mechanical vibration to generate a low-frequency shear wave inside a tissue and utilizes the ultrasonic waves to track the propagation of the shear wave inside the tissue, calculates related information such as the elasticity, attenuation of the tissue through measuring parameters of the shear wave. At present, the instantaneous elastography is mainly applied in the field of non-invasive detection of liver fibrosis, fatty livers, and the like.

In an existing instantaneous elastography device, typically, a vibration column passes through a center of a B-mode ultrasonic probe and an ultrasonic transducer array of a B-mode ultrasonic probe. The instantaneous elastography device utilizes vibration of the vibration column to generate a shear wave, and utilizes the ultrasonic transducer array around the vibration column to acquire detecting information of the shear wave, and acquires information such as the elasticity and an anatomical structure of the tissue through processing. However, the monitoring of the shear wave by such instantaneous elastography device is only performed by the ultrasonic transducer array around the vibration column. The monitored information contains both longitudinal displacements and lateral displacements, and the processing is complicated. Although the deficiency of the ultrasonic transducer array can be compensated by virtue of interpolation and beam forming and the like, the quality and accuracy of imaging will still be affected, and the amount of data processing will be increased.

SUMMARY

In order to at least partially solve the problems existing in the prior art, the present disclosure provides an acoustic lens, an ultrasonic probe provided with the acoustic lens and an ultrasonic detecting device provided with the ultrasonic probe.

An ultrasonic probe according to an aspect of the present disclosure, includes: an ultrasonic transducer array configured to transmit and receive ultrasonic waves; a conducting device disposed at a front end of the ultrasonic transducer array, where the conducting device includes a fluid chamber filled with fluid, and the fluid chamber has an opening and an energy receiving port which are in communication with each other, the opening is disposed on a front surface of the conducting device and covered by an elastic film; and an energy applying device, connected to the energy receiving port and configured to apply energy to the fluid within the fluid chamber to make the elastic film vibrate so as to generate a shear wave.

Preferably, the fluid is liquid.

Preferably, the fluid chamber is a column shape.

Preferably, the opening is of a circle or a stripe shape.

Preferably, the energy applying device includes an energy generating device and an energy transferring device, and the energy transferring device is connected between the energy generating device and the energy receiving port.

Preferably, the energy generating device includes one or more of a stepper motor, a linear vibrator, and a variable speed pump.

Preferably, the fluid chamber is adapted to the shape of the ultrasonic transducer array, and the fluid chamber is connected to a front end of the ultrasonic transducer array.

Preferably, the conducting device further includes an acoustic lens, the acoustic lens is connected to the front end of the ultrasonic transducer array, and the fluid chamber is disposed in the acoustic lens.

Preferably, a portion of the ultrasonic transducer array corresponding to a projection of the fluid chamber is connected to a first port, and other portion of the ultrasonic transducer array is connected to a second port, the first port is configured for instantaneous elastography, and the first port and the second port are configured for ultrasonic imaging.

An ultrasonic detecting device according to another aspect of the present disclosure, includes: a driving unit, connected to the energy applying device of the ultrasonic probe to drive the energy applying device; an ultrasonic unit, connected to the ultrasonic transducer array of the ultrasonic probe to control the ultrasonic transducer array to transmit and receive ultrasonic waves; and an elastography unit, connected to the ultrasonic transducer array for receiving and processing a first electrical signal containing shear wave information to perform instantaneous elastography.

Preferably, the elastography unit is connected to a portion of the ultrasonic transducer array corresponding to the projection of the fluid chamber.

Preferably, it is characterized in that the ultrasonic unit is further configured to perform ultrasonic imaging according to a second electrical signal received from the ultrasonic transducer array.

Preferably, the processing device further includes an integrated processing unit which is connected to the elastography unit and the ultrasonic unit so as to integrate processing results of the elastography unit and the ultrasonic unit.

Preferably, the integrated processing unit is further connected to the driving unit to control the driving unit.

Preferably, the ultrasonic detecting device further includes a displaying apparatus which is connected to the processing device.

The ultrasonic probe provided by the present disclosure adopts a complete ultrasonic transducer array to receive the ultrasonic signal including the shear wave information, therefore, it is unnecessary to compensate the acquired ultrasonic signal by virtue of interpolation and beam forming and the like, thus further improving the convenience and accuracy of the measurement, and reducing the processing difficulty. Thus it can be seen that the ultrasonic detecting device using the ultrasonic probe has many advantages, for example, good quality of imaging, small amount of data processing and high detection speed. In addition, it supports both of the function of the instantaneous elastography and the combined function of the traditional ultrasonic imaging (including traditional imaging and blood flow imaging) and the instantaneous elastography.

A series of concepts in a simplified form have been introduced in the summary of the disclosure, which will be described in further detail in the section of detailed description of embodiments. This summary of the disclosure is neither intended to limit the essential features and necessary technical features of the claimed technical solution, nor to determine the scope of protection of the claimed technical solution.

Advantages and features of the present disclosure will be described in detail below with reference to the accompanying drawings.

BRIEF DESCRIPTION OF DRAWINGS

Following drawings of the present disclosure are incorporated herein as part of the present disclosure for understanding the present disclosure. The drawings illustrate embodiments of the disclosure and the description thereof to explain the principles of the disclosure. In the drawings.

DETAILED DESCRIPTION OF EMBODIMENTS

Numerous details are provided in the following description so that the present disclosure can be thoroughly understood. However, those skilled in the art will appreciate that the following description merely exemplarily illustrates preferred embodiments of the present disclosure, and the present disclosure may be practiced without one or more of these details. In addition, some technical features that are well known in the art are not described in detail in order to avoid confusion with the present disclosure.

Figure 1:
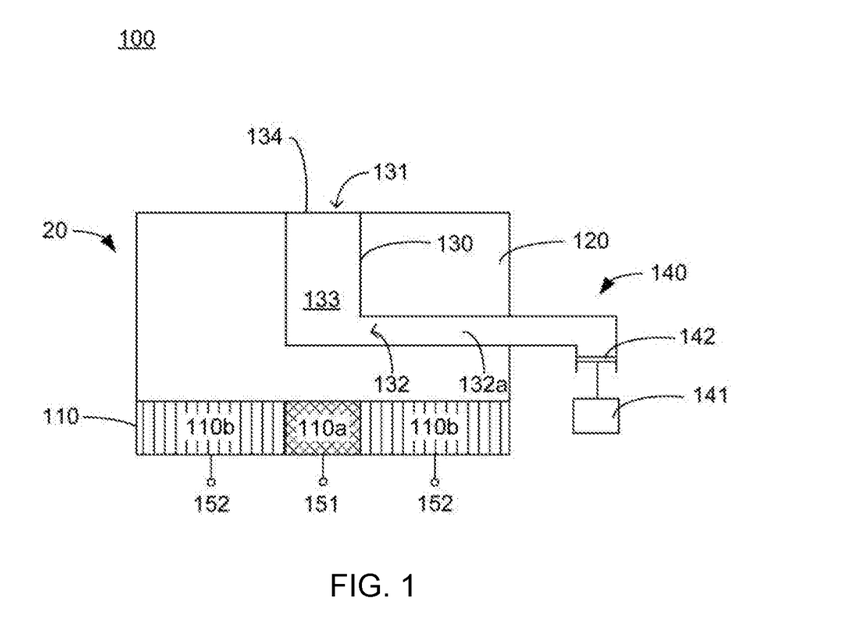
FIG. 1 is a sectional view of an ultrasonic probe according to an embodiment of the present disclosure.
Figure 2:
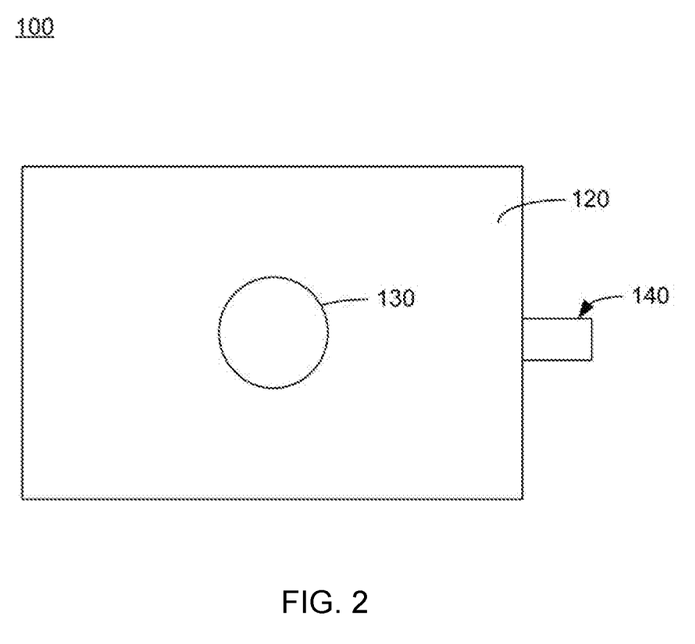
FIG. 2 is a top view of an ultrasonic probe according to an embodiment of the present disclosure.
Figure 3:
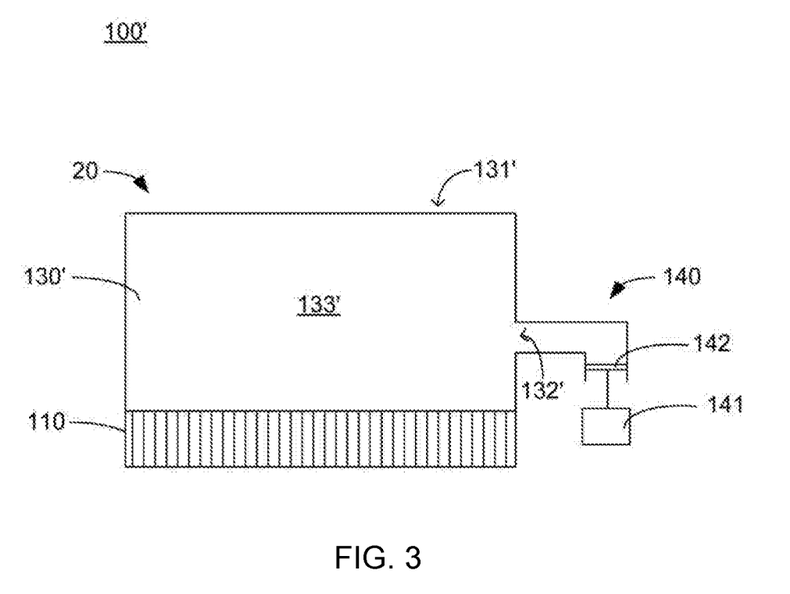
FIG. 3 is a sectional view of an ultrasonic probe according to another embodiment of the present disclosure.

An ultrasonic probe is provided according to an aspect of the present disclosure. FIG. 1 and FIG. 2 respectively show a sectional view and a top view of an ultrasonic probe according to an embodiment of the present disclosure. FIG. 3 shows a sectional view of an ultrasonic probe according to another embodiment of the present disclosure. The ultrasonic probe provided by the present disclosure will be described in detail with reference to FIGS. 1-3. As shown in FIGS. 1-3, the ultrasonic probe 100 includes an ultrasonic transducer array 110, a conducting device 20 and an energy applying device 140.

Ultrasonic transducer array 110 is configured to transmit and receive the ultrasonic waves. The ultrasonic transducer array 110 performs electrical-acoustic conversion on the transmitted signal to transmit an ultrasonic signal to a tissue, receives the ultrasonic echo signal reflected by the tissue and performs acoustic-electrical conversion to generate a received signal. The received signal may include shear wave information. Optionally, the received signal may also include tissue information. The tissue information may include information such as anatomic information and/or blood flow information of the tissue for the use in traditional ultrasonic imaging (herein referred to as ultrasonic imaging). The ultrasonic image includes a two-dimensional ultrasonic image acquired based on the anatomic information, and/or blood flow image of the tissue acquired based on the blood flow information, and the like. In one embodiment, the ultrasonic transducer array 110 may be any one or more of a linear array ultrasonic transducer, a convex array ultrasonic transducer, a phased array ultrasonic transducer and a two-dimensional (2D) ultrasonic transducer. Ultrasonic transducer array 110 may be configured to monitor the shear wave, however, optionally, ultrasonic transducer array 110 may also be configured for traditional imaging or blood flow imaging when properly configured.

The conducting device 20 is disposed at the front end of the ultrasonic transducer array 110. The conducting device 20 includes a fluid chamber 130 filled with fluid. The fluid chamber 130 is configured to be filled with fluid 133. The fluid 133 is mainly configured to transfer energy, especially vibration (which will be described in detail below), and therefore, the term "fluid" referred to in the present disclosure is intended to cover all substances capable of transferring energy (especially vibration). In general, fluid 133 includes gas or liquid. Because the fluid chamber 130 is disposed on the transfer path of the ultrasonic energy and the attenuation velocity of ultrasonic energy is faster in gas than in liquid, it is preferable that the fluid is liquid. In a preferred embodiment, fluid 133 is water.

The fluid chamber 130 has an opening 131 and an energy receiving port 132, and the opening 131 and the energy receiving port 132 are in communication with each other. The opening 131 is disposed on the front surface of the conducting device 20 (i.e., the upper surface shown in FIG. 1). The front surface of the conducting device 20 refers to the surface of the conducting device 20 that is in contact with a body surface of a human or an animal. The opening 131 is covered by an elastic film 134. The elastic film 134 may be a film made of various elastic materials. The energy receiving port 132 is in communication with the opening 131. The energy receiving port 132 is configured to receive energy. The energy received by the energy receiving port 132 reaches the elastic film 134 after being transferred via the fluid in the fluid chamber 130, causes the elastic film 134 to vibrate and generate a shear wave, and the ultrasonic waves are utilized to trace the propagation of the shear wave inside the tissue, so as to perform instantaneous elastography and acquire elasticity information and attenuation information of the tissue. The structure and position of the energy receiving port 132 are not limited by the accompanying figures. The energy receiving port 132 is configured to be connected to the energy applying device 140 to receive the energy provided by the energy applying device 140. The structure of the energy receiving port 132 may be designed to be adapted to the energy output end of the energy applying device 140. The energy receiving port 132 may be disposed at any position such as sides, the bottom, or the top of the fluid chamber 130 as long as it functions. The energy receiving port 132 may include an extension 132a to transfer the energy provided by the energy applying device 140 to the fluid within the fluid chamber 130. Those skilled in the art can understand that, the energy receiving port 132 may not include the extension 132a in some cases, for example, when the fluid chamber 130 is disposed near the edge of the conducting device 20 or the lateral (i.e., the horizontal direction shown in FIG. 1) dimension of the fluid chamber 130 is relatively large. In addition, the energy output end of the energy applying device 140 may also be designed to be extended into the conducting device 20, in this case, the energy receiving port 132 may also not include the extension 132*a*. However, the energy output end of the energy applying device 140 being extended in to the conducting device 20 may cause the ultrasonic waves transmitted and received by the ultrasonic transducer array 110 to encounter the gaseous medium while propagating in the conducting device 20, and thereby attenuating the energy of the ultrasonic waves.

The energy applying device 140 is connected to the energy receiving port 132 for applying energy to the fluid 133 within the fluid chamber 130. The energy is transferred to the elastic film 134 via the fluid 133 so that the elastic film 134 vibrates and generates a shear wave. The shear wave propagates from the body surface to the inside of the tissue to cause tiny deformation of the biological tissue by means of external or internal forces. After the shear wave is transmitted, ultrasonic waves are transmitted by the ultrasonic transducer array 110, the ultrasonic waves are utilized to trace the propagation of the shear wave inside the tissue so that the parameters of the shear wave are measured, and further related information such as the elasticity and attenuation of the tissue is calculated. As an example, the shear wave frequency may range from 10 Hz to 1000 Hz. The amplitude of the shear wave may range from 0.2 mm to 5 mm.

The ultrasonic probe provided by the present disclosure adopts a complete ultrasonic transducer array to receive the ultrasonic signal including the shear wave information, therefore, it's unnecessary to compensate the acquired ultrasonic signal by virtue of interpolation and beam forming and the like, thus further improving the convenience and accuracy of the measurement, and reducing the processing difficulty. Thus it can be seen that the ultrasonic detecting device using the ultrasonic probe has many advantages, for example, good quality of imaging, small amount of data processing and high detection speed. In addition, it supports both of the function of the instantaneous elastography and the combined function of the traditional ultrasonic imaging (including traditional imaging and blood flow imaging) and the instantaneous elastography.

In one embodiment, as shown in FIGS. 1-2, the conducting device 20 may further include an acoustic lens 120 in addition to the fluid chamber 130. The acoustic lens 120 is connected to the front end of the ultrasonic transducer array 110. The fluid chamber 130 is disposed in the acoustic lens 120. The acoustic lens 120 may surround the fluid chamber 130 from the side and bottom surfaces of the fluid chamber 130 as shown in FIG. 1. In other embodiments that are not shown, the acoustic lens 120 may surround the fluid chamber 130 only from the side surfaces of the fluid chamber 130. In this case, the bottom surface of the fluid chamber 130 is in contact with the ultrasonic transducer array 110. The opening 131 of the fluid chamber 130 is disposed on the front surface of the acoustic lens 120. When in use, the acoustic lens 120 is in contact with the body surface of the human or animal. In order to increase the detection sensitivity, that is, to increase the sound pressure in the measured area, a focusing acoustic lens may be used. The acoustic lens 120 can be made of any sound-permeable material, such as silicone rubbers, room temperature vulcanized rubbers and high-temperature vulcanized rubbers. The fluid chamber 130 may have various shapes instead of being limited to the shapes shown in the drawings. That is, fluid chambers 130 of various shapes that are capable of achieving the above-mentioned functions are all included in the protection scope of the present disclosure. In addition, although only one fluid chamber 130 is shown in FIGS. 1-2, the acoustic lens 120 may be provided with a plurality of fluid chambers. Exemplarily, the plurality of fluid chambers may be disposed in a straight line in the acoustic lens 120 or be disposed in a form of two-dimensional matrix in the acoustic lens 120. The plurality of fluid chambers may be disposed in any other suitable manner in the acoustic lens 120 as desired and/or required.

In another embodiment, as shown in FIG. 3, a fluid chamber 130' is connected to a front end of an ultrasonic transducer array 110. In this embodiment, an acoustic lens is omitted. The fluid chamber 130' is adapted to the shape of the ultrasonic transducer array 110. An opening 131' of the fluid chamber 130' is disposed on the front surface of the fluid chamber 130'. When in use, the front surface of fluid chamber 130' is in contact with the body surface of the human or animal. The opening 131' may be disposed on the entire front surface of the fluid chamber 130' or on a portion of the front surface. The energy receiving port 132' is in communication with the opening 131'. The energy receiving port 132' is connected to the energy applying device 140 to receive the energy provided by the energy applying device 140. In this embodiment, same reference numerals are used to denote components that are the same as or similar to those of the previous embodiment, and the same or similar components will not be described in further detail herein.

In various embodiments described above, preferably, the fluid chambers 130 and 130' may be of a column shape. The column has a consistent cross section along the propagation direction of the ultrasonic waves, and the cross section of the cylinder can be circular, semicircular, polygonal, etc. By providing the fluid chambers 130 and 130' of a column shape, on one hand, the energy loss due to collision with the side walls of the fluid chambers 130 and 130' during transfer of energy may be avoided; on the other hand, the increased calculation difficulty in imaging due to the ultrasonic waves or vibration being reflected or refracted by sidewalls of the fluid chambers 130 and 130' during the transfer may be avoided.

The ultrasonic probe of the current instantaneous elastography device is mainly configured to detect elasticity information, attenuation information, and the like of the liver, and the ultrasonic probe is mainly placed at the surface of the inter costal space when it works, and the sizes of the openings 131 and 131' of the fluid chamber 130 are typically designed to be relatively small. In a preferred embodiment, the openings 131 and 131' of the fluid chamber 130 may be circular so as to perform spot measurements on the detecting area. In another preferred embodiment, the openings 131 and 131' of the fluid chamber 130 may be of a strip shape to perform a plane measurement suitable for inter costal detecting.

Optionally, as shown in FIG. 1 and FIG. 3, the energy applying device 140 may include an energy generating device 141 and an energy transferring device 142. The energy transferring device 142 is connected between the energy generating device 141 and the energy receiving ports 132 and 132'. In an embodiment, the energy generating device 141 may include one or more of a stepper motor, a linear vibrator and a variable speed pump. In an embodiment, the energy generating device 141 is configured to generate low-frequency vibrations that are transferred through energy transferring device 142 to the fluid within fluid chambers 130 and 130'. The energy generating device 141 may be assembled inside a housing (not shown) of the ultrasonic probe 100, or be disposed outside the housing of the ultrasonic probe 100 as long as the energy can be outputted to the energy receiving ports 132 and 132' through the energy transferring device 142. A direct or indirect way of energy transferring may be adopted by the energy transferring device 142 to transfer the vibration generated by the energy generating device 141 to the fluid 133 and 133'. The energy transferring device 142 is hermetically connected to the energy receiving ports 132 and 132'. The energy transferring device 142 may be a mechanical linkage in any form as long as the energy outputted by the energy generating device 141 can be transferred to the fluid 133 and 133'.

The above-mentioned ultrasonic probe provided by the present disclosure can be configured for instantaneous elastography, and can also be configured for image-guided instantaneous elastography. The instantaneous elastography based on image-guide combines the functions of instantaneous elastography with the functions of traditional ultrasonic imaging (i.e., ultrasonic imaging). Instantaneous elastography is used to acquire information such as elasticity and attenuation a tissue. Ultrasonic imaging is used to acquire information such as an anatomical structure of a tissue, internal fluid velocity, etc. The acquired anatomical structure information plays a guiding role in the measurement of elasticity related information. In actual use, ultrasonic imaging may be utilized first to acquire a two-dimensional ultrasonic image of a biological tissue in real time by moving the ultrasonic probe so as to assist and guide the ultrasonic probe to perform precise positioning on the tissue according to actual requirements; then switch to instantaneous elastography for the elasticity detecting. Ultrasonic imaging and instantaneous elastography can also be performed simultaneously as required and/or desired.

In the case where the ultrasonic probe combines the function of instantaneous elastography with the function of traditional ultrasonic imaging, for the embodiment shown in FIGS. 1-2, the portion 110a of the ultrasonic transducer array 110 corresponding to the projection of the fluid chamber 133 is configured to receive the ultrasonic signal including shear wave information, and the ultrasonic signal is configured to instantaneous elastography; and the entire ultrasonic transducer array 110 may be configured to receive the ultrasound signal containing anatomic information and/or blood flow information, and the ultrasonic signal is configured for ultrasonic imaging. The portion 110 of the ultrasonic transducer array 110 corresponding to the projection of the fluid chamber 133 is connected to the first port 151. Other portion 110b of the ultrasonic transducer array 110 is connected to the second port 152. In this way, the first port 151 may be configured for instantaneous elastography; and the first port 151 and the second port 152 may be configured for ultrasonic imaging. Implementation and application of the functions of instantaneous elastography and ultrasonic imaging will be described in detail later. The ultrasonic probe of the preferred embodiment includes both the functions of a traditional ultrasonic imaging probe and more importantly the functions of instantaneous elastography, which enables the measurement of tissue elasticity. It is unnecessary to switch between two probes when in use, which is very convenient for the operator.

In the case where the ultrasonic probe integrates the functions of both instantaneous elastography and traditional ultrasonic imaging, for the embodiment shown in FIG. 3, the first port and the second port may not be distinguished, that is, the port connected with each part of the ultrasonic transducer array 110 may be configured for both instantaneous elastography and ultrasonic imaging.

Figure 4:
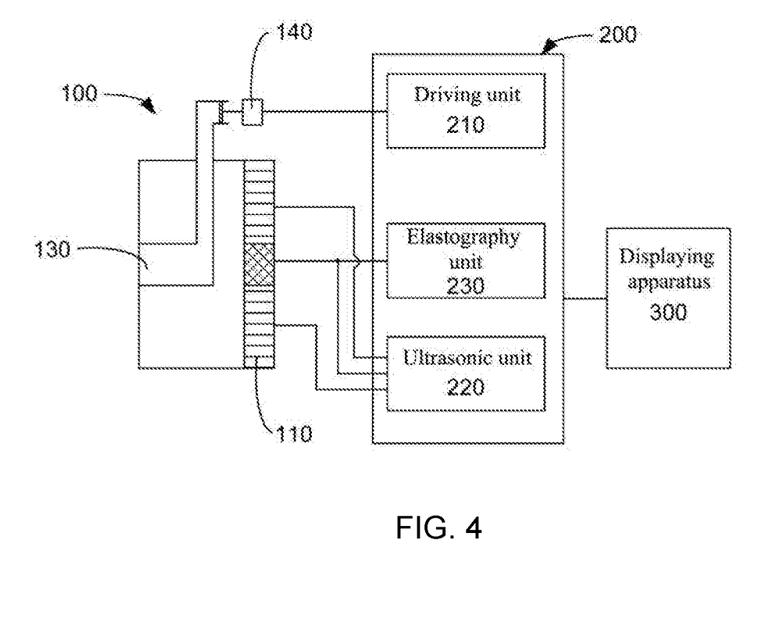
FIG. 4 is a schematic block diagram of an ultrasonic detecting device according to an embodiment of the present disclosure.

According to another aspect of the present disclosure, an ultrasonic detecting device is also provided. FIG. 4 illustrates a schematic block diagram of an ultrasonic detecting device according to an embodiment of the present disclosure. As shown in FIG. 4, the ultrasonic detecting device includes an ultrasonic probe 100 and a processing device 200.

The ultrasonic probe 100 may have any one of the above-mentioned structures, and the structure of the ultrasonic probe 100 will not be described in further detail here for simplicity. Only the ultrasonic probe 100 shown in FIGS. 1-2 is taken as an example to illustrate the principle of the ultrasonic detecting device in FIG. 4. However, those skilled in the art will understand that the ultrasonic detecting device may also adopt the ultrasonic probe shown in FIG. 3.

The processing device 200 may include a driving unit 210, an ultrasonic unit 220, and an elastography unit 230.

The driving unit 210 is connected to the energy applying device 140 of the ultrasonic probe 100 to drive the energy applying device 140. The driving unit 210 drives the energy applying device 140 to pressurize the fluid in the fluid chamber 130 to drive the elastic film of the fluid chamber 130 vibrate so as to generate the shear wave.

The ultrasonic unit 220 is connected to the ultrasonic transducer array 110 of the ultrasonic probe 100 to control the ultrasonic transducer array 110 to transmit and receive ultrasonic waves. After the driving unit 210 drives the ultrasonic probe 100 to transmit the shear wave, the ultrasonic unit 220 drives the ultrasonic transducer array 110 to transmit the ultrasonic waves into the biological tissue according to loaded imaging parameters. The ultrasonic waves may track the propagation of the shear wave within the tissue, and the ultrasonic transducer array 110 receives a reflected first ultrasonic signal (i.e., ultrasonic echo) that includes shear wave information. The ultrasonic transducer array 110 converts the first ultrasonic signal into a first electrical signal which contains the shear wave information. In a specific embodiment, the ultrasonic unit 220 may include an ultrasonic transmitting module, an ultrasonic receiving module and a transmitting-receiving switch circuit. Wherein, the ultrasonic transmitting module is configured to control the ultrasonic transducer array 110 to transmit the ultrasonic signal; the ultrasonic receiving module is configured to control the ultrasonic transducer array 110 to receive the ultrasonic echo signal; and the transmitting-receiving switch circuit is configured to isolate high voltage.

The elastography unit 230 is connected to the ultrasonic transducer array 110 of the ultrasonic probe 100 so as to receive the first electrical signal containing the shear wave information and to process the first electrical signal for instantaneous elastography. The instantaneous elastography is used to acquire elasticity information and/or attenuation information, and the like of the tissue.

Preferably, the elastography unit 230 is connected to a portion of the ultrasonic transducer array 110 corresponding to the projection of the fluid chamber 130 (e.g. 110a in FIG. 1). Optionally, the elastography unit 230 may also be connected to the entire ultrasonic transducer array 110 or any other part of the ultrasonic transducer array 110 so as to receive the first electrical signal containing the shear wave information. However, in the preferred embodiment (i.e., where the elastography unit 230 is connected to 110a), the first ultrasonic signal received through the 110a includes information related to the shear wave propagation, and elasticity information, attenuation information, and the like of the tissue may be acquired by processing the first ultrasonic signal without the requirements of complex processing such as interpolation or beam forming. It can be understood that in the embodiment shown in FIG. 3, since the shape of the ultrasonic transducer array 110 and that of the fluid chamber 130 are adapted to each other, the elastography unit 230 may also be connected to the entire ultrasonic transducer arrays 110 so as to receive the first electrical signal from the entire ultrasonic transducer array 110. And of course, optionally, the elastography unit 230 may also be connected to only a portion of the ultrasonic transducer array 110.

In the ultrasonic detecting device provided by the present disclosure, a complete ultrasonic transducer array is configured to receive an ultrasonic signal including shear wave information, requiring no compensation for the acquired ultrasonic signal by interpolation, beam forming, etc., thereby improving convenience and accuracy of measurement of a tissue and reducing the difficulty of processing. It can be seen that the ultrasonic detecting device has many advantages such as good imaging quality, small data processing amount, and fast detecting speed.

In a preferred embodiment, the ultrasonic unit 220 is further configured to perform ultrasonic imaging based on a second electrical signal received from the ultrasonic transducer array 110. The ultrasonic transducer array 110 transmits ultrasonic waves configured for traditional ultrasonic imaging into the tissue and receives a reflected second ultrasonic signal (i.e., the ultrasonic echo). The second ultrasonic signal includes tissue anatomic information and/or blood flow information of a tissue. The ultrasonic transducer array 110 converts the second ultrasonic signal into a second electrical signal which is provided to the ultrasonic unit 220 for ultrasonic imaging. For the processing function of the second electrical signal of the ultrasonic unit 220 is similar to the ultrasonic imaging unit in a traditional ultrasonic imaging device. The processing includes, for example, one or more of beam forming, demodulation, compression, blood flow estimation, spectrum calculation, DSC conversion, and the like. The ultrasonic imaging is used to acquire information such as anatomy and blood flow of the tissue. The ultrasonic detecting device of this preferred embodiment includes both the functions of the traditional ultrasonic imaging and, more importantly, the function of supporting instantaneous elastography. It's unnecessary to switch between two probes when in use, which is very convenient for the operator.

Figure 5:
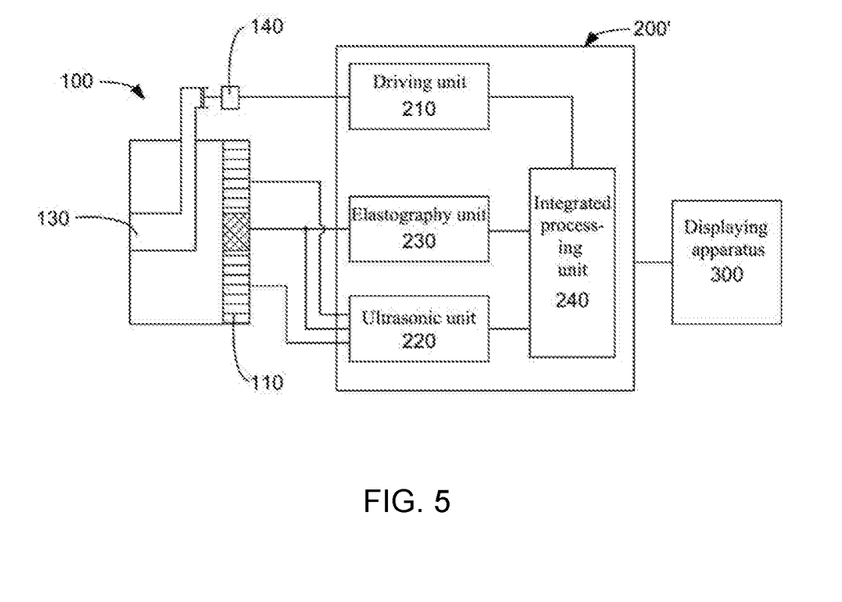
FIG. 5 is a schematic block diagram of an ultrasonic detecting device according to another embodiment of the present disclosure.

In a preferred embodiment, as shown in FIG. 5, the processing device 200 further includes an integrated processing unit 240. Except for this, the ultrasonic detecting device shown in FIG. 5 is basically the same as the ultrasonic detecting device in the foregoing embodiments, so the same reference numerals are used in FIG. 5 for the same or similar components which will not be described in further detail. The integrated processing unit 240 is connected to the elastography unit 230 and the ultrasonic unit 220. The integrated processing unit 240 may integrate the processing results of the elastography unit 230 and the ultrasonic unit 220 to provide various biological tissue information including elasticity, attenuation, anatomical Structure, blood flow, and the like of the tissue. Optionally, the integrated processing unit 240 may also provide the ultrasonic unit 220 and the elastography unit 230 with parameter controlling of ultrasonic imaging. Exemplarily, the integrated processing unit 240 may perform calculating according to parameters such as ultrasonic wave propagation speed, array element spacing and the detecting depth, so as to control aspects of the ultrasonic transducer array 110 such as start time, stop time, pulse width and pulse repetition rate through the ultrasonic unit 220 and the elastography unit 230.

In a further preferred embodiment, the integrated processing unit 240 is further connected to the driving unit 210 for controlling the driving unit 210. As an example, the integrated processing unit 240 may control the amplitude, frequency and time of vibration generated by the energy applying device 140 which is driven by the driving unit 210.

In one embodiment, the ultrasonic detecting device further includes a displaying apparatus 300 connected to the processing device 200, as shown in FIGS. 4-5. The displaying apparatus 300 is configured to display a two-dimensional ultrasonic image, a blood flow image, and/or elasticity information, attenuation information, and the like of a tissue. Optionally, the displaying apparatus 300 may be connected to the integrated processing unit 240 to display processing result calculated by the integrated processing unit 240. Optionally, in the embodiment where the processing device 200 does not include the integrated processing unit 240, the displaying apparatus 300 may be directly connected to the elastography unit 230 and/or the ultrasonic unit 220 to directly display the processing result of the elastography unit 230 and/or the ultrasonic unit 220.

The present disclosure has been described with reference to the above embodiments, but it should be understood that the above described embodiments are for the purpose of illustration and description only and are not intended to limit the present disclosure to the scope of the described embodiments. In addition, those skilled in the art can understand that the present disclosure is not limited to the foregoing embodiments, and various variations and modifications can be made according to the teachings of the present disclosure, and these variations and modifications all fall within the protection scope claimed by the disclosure. The protection scope of the disclosure is defined by the appended claims and their equivalents.

What is claimed is:

1. An ultrasonic probe, comprising:
an ultrasonic transducer array configured to transmit and receive ultrasonic waves;
a conducting device disposed at a front end of the ultrasonic transducer array, wherein the conducting device comprises a fluid chamber filled with liquid, and the fluid chamber has an opening and an energy receiving port which are in communication with each other, and the opening is disposed on a front surface of the conducting device and covered by an elastic film; and
an energy applying device, connected to the energy receiving port and configured to apply vibrations to the liquid within the fluid chamber,
wherein the energy receiving port is configured to receive the vibrations, the vibrations received by the energy receiving port reaches the elastic film after being transferred via the liquid in the fluid chamber, and causes the elastic film to vibrate and generate a shear wave propagating from a body surface to an inside of a tissue, and the ultrasonic waves are utilized to trace the propagation of the shear wave inside the tissue, so as to perform instantaneous elastography and acquire at least one of elasticity information and attenuation information of the tissue,
wherein the conducting device further comprises an acoustic lens, the acoustic lens is connected to the front end of the ultrasonic transducer array, and the acoustic lens surrounds the fluid chamber from side surface of the fluid chamber;

wherein a first portion of the ultrasonic transducer array corresponding to a projection of the fluid chamber is configured to receive an ultrasonic signal including shear wave information.

2. The ultrasonic probe according to claim 1, wherein the fluid chamber is of a column shape.

3. The ultrasonic probe according to claim 1, wherein the opening is of a circle or a stripe shape.

4. The ultrasonic probe according to claim 1, wherein the energy applying device comprises an energy generating device and an energy transferring device, and the energy transferring device is connected between the energy generating device and the energy receiving port.

5. The ultrasonic probe according to claim 4, wherein the energy generating device comprises one or more of a stepper motor, a linear vibrator, and a variable speed pump.

6. The ultrasonic probe according to claim 1, wherein the fluid chamber is adapted to the shape of the ultrasonic transducer array, and the fluid chamber is connected to the front end of the ultrasonic transducer array.

7. The ultrasonic probe according to claim 1, wherein the first portion of the ultrasonic transducer array corresponding to the projection of the fluid chamber is connected to a first port, and a second portion of the ultrasonic transducer array is connected to a second port, the first port is configured for instantaneous elastography, and the first port and the second port are configured for ultrasonic imaging.

8. The ultrasonic probe according to claim 7, wherein the first portion of the ultrasonic transducer array corresponding to the projection of the fluid chamber and the second portion of the ultrasonic transducer array are configured to receive the ultrasound signal containing anatomic information and/or blood flow information.

9. An ultrasonic detecting device, wherein the ultrasonic detecting device comprises:
the ultrasonic probe according to claim 1; and
a processing device, which comprises:
a driving unit, connected to the energy applying device of the ultrasonic probe to drive the energy applying device;
an ultrasonic unit, connected to the ultrasonic transducer array of the ultrasonic probe to control the ultrasonic transducer array to transmit and receive the ultrasonic waves; and
an elastography unit, connected to the ultrasonic transducer array for receiving and processing a first electrical signal containing shear wave information to perform the instantaneous elastography.

10. The ultrasonic detecting device according to claim 9, wherein the elastography unit is connected to the first portion of the ultrasonic transducer array corresponding to the projection of the fluid chamber.

11. The ultrasonic detecting device according to claim 9, wherein:
the ultrasonic unit is further configured to perform ultrasonic imaging according to a second electrical signal received from the ultrasonic transducer array.

12. The ultrasonic detecting device according to claim 11, wherein the processing device further comprises an integrated processing unit which is connected to the elastography unit and the ultrasonic unit so as to integrate processing results of the elastography unit and the ultrasonic unit.

13. The ultrasonic detecting device according to claim 12, wherein the integrated processing unit is further connected to the driving unit to control the driving unit.

14. The ultrasonic detecting device according to claim 9, wherein the ultrasonic detecting device further comprises a displaying apparatus which is connected to the processing device.

15. The ultrasonic detecting device according to claim 9, wherein the energy applying device comprises an energy generating device and an energy transferring device, and the energy transferring device is connected between the energy generating device and the energy receiving port.

16. The ultrasonic detecting device according to claim 9, wherein the fluid chamber is adapted to the shape of the ultrasonic transducer array, and the fluid chamber is connected to the front end of the ultrasonic transducer array.

17. The ultrasonic detecting device according to claim 9, wherein the first portion of the ultrasonic transducer array corresponding to the projection of the fluid chamber is connected to a first port, and a second portion of the ultrasonic transducer array is connected to a second port, the first port is configured for instantaneous elastography, and the first port and the second port are configured for ultrasonic imaging.

18. The ultrasonic probe according to claim 1, wherein the entire ultrasonic transducer array is capable of receiving an ultrasound signal including tissue information, wherein the tissue information includes anatomic information and/or blood flow information of the tissue; and the first portion of the ultrasonic transducer array corresponding to the projection of the fluid chamber is capable of receiving both the ultrasound signal including the tissue information and the ultrasonic signal including the shear wave information.

* * * * *